United States Patent [19]

Naser et al.

[11] 4,381,789
[45] May 3, 1983

[54] ELECTRODE SYSTEM

[75] Inventors: Georg Naser, Zirndorf; Franz Strahwald, Ebermannstadt; Erich Szehi, Buckenhof, all of Fed. Rep. of Germany

[73] Assignee: Siemens Aktiengesellschaft, Berlin & Munich, Fed. Rep. of Germany

[21] Appl. No.: 203,431

[22] Filed: Nov. 3, 1980

[30] Foreign Application Priority Data

Nov. 20, 1979 [DE] Fed. Rep. of Germany ... 7932779[U]

[51] Int. Cl.³ .............................................. A61N 1/04
[52] U.S. Cl. .................................................. 128/798
[58] Field of Search .............................. 128/639–641, 128/643, 644, 783, 798, 799, 802, 803

[56] References Cited

U.S. PATENT DOCUMENTS

| 3,340,868 | 9/1967 | Darling | 128/640 |
| 3,380,445 | 4/1968 | Frasier | 128/639 |
| 3,888,240 | 6/1975 | Reinhold, Jr. et al. | 128/644 |
| 4,023,574 | 5/1977 | Nemec | 128/420 A |
| 4,051,842 | 10/1977 | Hazel et al. | 128/640 |
| 4,082,086 | 4/1978 | Page et al. | 128/640 |
| 4,082,087 | 4/1978 | Howson | 128/640 |

FOREIGN PATENT DOCUMENTS

| 759 | 2/1979 | European Pat. Off. | 128/643 |
| 394385 | 1/1923 | Fed. Rep. of Germany | 128/798 |
| 2735050 | 2/1979 | Fed. Rep. of Germany | 128/640 |
| 1288323 | 9/1972 | United Kingdom | 128/798 |

Primary Examiner—Lee S. Cohen
Attorney, Agent, or Firm—Hill, Van Santen, Steadman, Chiara & Simpson

[57] ABSTRACT

In the exemplary embodiments, a multiple electrode for interference current therapy includes individual contact parts for emplacement on the patient at the location of application, and from which connection lines lead to the operational apparatus, or the like. In order to guarantee as simple as possible an application of the electrode system, an extended area-flexible formed part of electrically insulating plastic has flexible, electrically conductive plastic parts, as electrode contact parts, embedded in a smooth fashion. A good adaptation of the electrode system to different contours of the application location on the patient's body thus results.

15 Claims, 5 Drawing Figures

ELECTRODE SYSTEM

BACKGROUND OF THE INVENTION

The invention relates to an electrode system for the supply or pickup of electric signals; in particular, an electrode system as a multiple electrode for interference current-therapy, comprised of a housing serving as the support of the electrode contact parts for the purpose of placement on the patient at the application location, as well as comprising a connecting line to the contact parts which leads from the housing in a common line to an operating apparatus, or the like.

Electrode arrangements of this type make possible the supply of electric signals to a patient's body; for example, stimulation currents in the case of stimulation current treatment. However, electrode systems of this type can also be employed for tapping bioelectric signals, such as EKG, or the like, from a body. However, what is essential, in any case, is that during application the electrode contact parts have good contact on the body of the patient, so that signals can be supplied to the patient's body in as interference-free fashion as possible, or so that they can be tapped from the patient's body via the electrode in an interference-free fashion.

Particularly, in the case of multi-circuit stimulation current treatment, it is important to apply the individual current circuits, via the electrode system, at very specific locations of the patient's body. In addition to the separate application of individual electrode contact parts, frequently so-called electrode-sets are already being employed for this purpose in which the required number of electrode contact parts is already interconnected in a prescribed geometry. This has the advantages for routine operation, since only one or two electrode-sets in each instance need be applied on the body section of the patient to be treated.

Specifically in the utilization of three current circuits for obtaining a stereo interference effect of the stimulation current, electrode systems are, for example, employed in a so-called star configuration, but also in a series configuration. In order that such electrode sets can be mounted on any desired application location of the patient's body, the sets must be flexible per se. Therefore, flexible wire gauze inserts as electrode contact parts have hitherto most frequently been inserted in cellular rubber supports, whereby the entire contact surface was preferably covered with a viscose sponge cloth. The disadvantage of arrangements of this type is that most often the desired flexibility was not obtained. In the individual instance, due to the largely exposed wire gauzes, the danger of burnings if a wire were to break or become detached and wire ends were to pierce through, could not be precluded.

SUMMARY OF THE INVENTION

Accordingly, it is the object of the invention to disclose an electrode system for stimulation current treatment which is further improved with regard to the safety and comfort of application. In particular, the danger of burnings due to exposed wire ends, or the like, is to be entirely eliminated.

The object is achieved in accordance with the invention in that the housing is a relatively flat, flexible formed part consisting of electrically insulating plastic in which, as the electrode contact parts, flexible, electrically conductive plastic parts are embedded in a smooth fashion.

The inventive electrode system has the advantage of a largely constant flexibility. The insulating plastic formed part and contact parts form, through vulcanization in the direction of the application surface, a smooth surface which is closed on all sides. A simple and reliable cleansing and disinfection of the entire electrode system is therefore possible.

Preferably the conductive contact part is connected with a wire gauze at the rear side for the purpose of improved current distribution. During manufacture of the electrode system, such a wire gauze is first vulcanized on or into the conductive plastic, before such inserts are inserted in the formed part, consisting of nonconductive plastic, and once again intimately interconnected by means of thermal treatment. The contact inserts can here readily project out in relation to the flat part, so that they always with certainty rest against the body surface. A continuous spline beading is formed about the contact part in the insulating formed part which serves the purpose of improved anchoring in the formed part.

In a design as a triple electrode the contact parts are preferably arranged in lobes each offset by 120°. In this manner, a star-shaped electrode is formed. However, the contact parts can also be arranged in tandem in a band-shaped areal (or laminar) form. The form and size of the entire electrode system are adapted for the respective requirement for utilization on various body parts.

The electrode systems can exhibit an integrated line terminal for an operating cable with an operating plug connector. However, a plug and socket connection can also be directly provided on the electrode system which, in particular, serves the purpose of rapid exchange of the electrode sets.

Since the operating cable is generally designed in the form of a flat wire conductor, and since the electric connections in the formed part consist of temperature-resistant Teflon-covered lines, a coupling part is provided for the purpose of connection. In the latter, the individual lines can be fixedly connected (crimped) with the flat wire conductors of the operating cable. The coupling part can simultaneously exhibit a pull (or tension) relief for the cable.

Further advantages and details of the invention shall be apparent from the following figure description of exemplary embodiments on the basis of the accompanying drawing sheets in conjunction with the remaining subclaims; and other objects, features and advantages will be apparent from this detailed disclosure and from the appended claims.

DETAILED DESCRIPTION

Figures 1, 2:
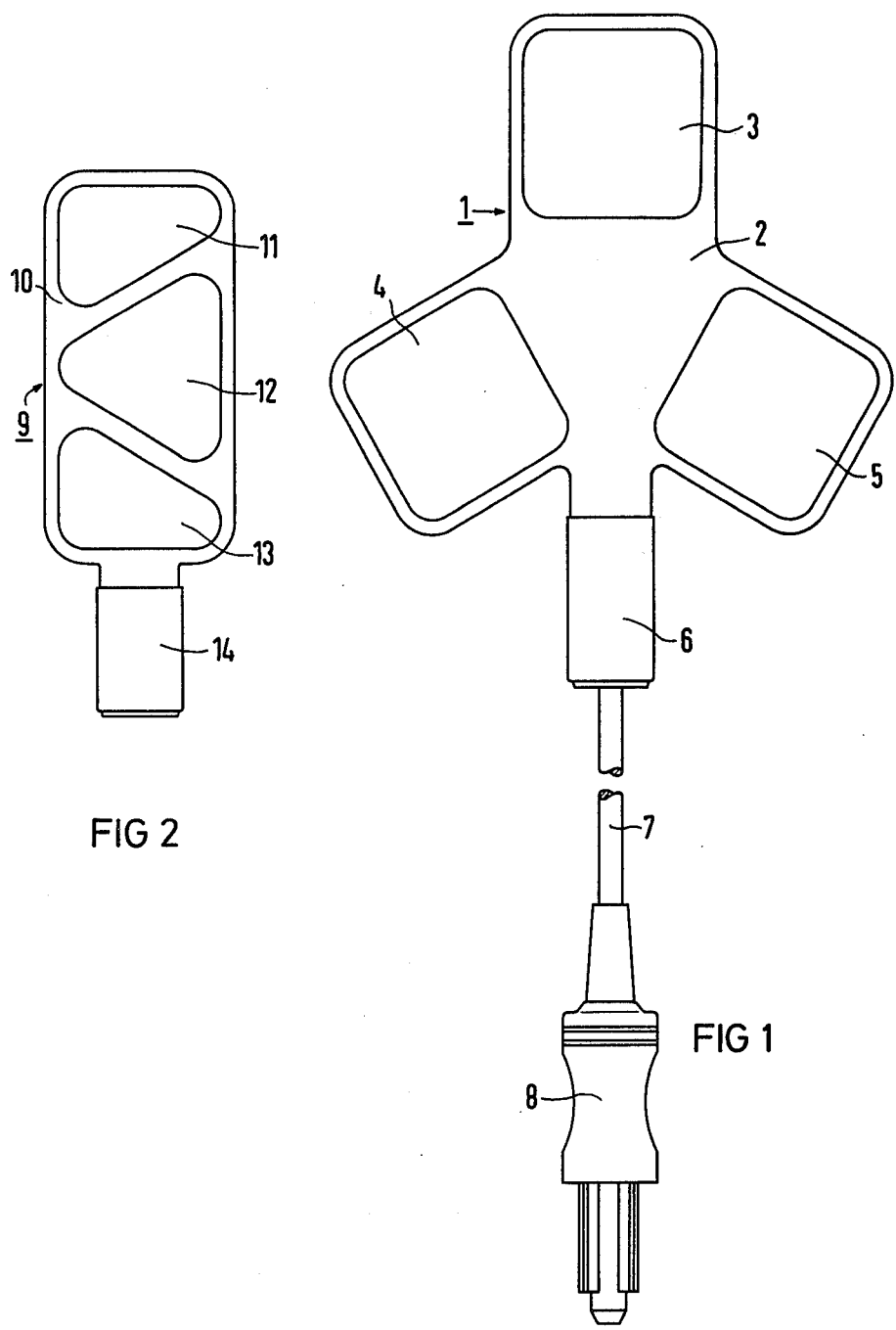
FIG. 1 illustrates a plan view of the application side of an inventively designed star electrode system.
FIG. 2 illustrates a corresponding view of a band-shaped configuration triple electrode system.
Figure 4:
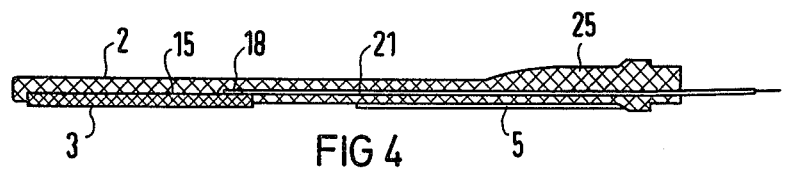
FIG. 4 illustrates a section through the arrangement of FIG. 3, taken along the line IV—IV of FIG. 3.
Figure 3:
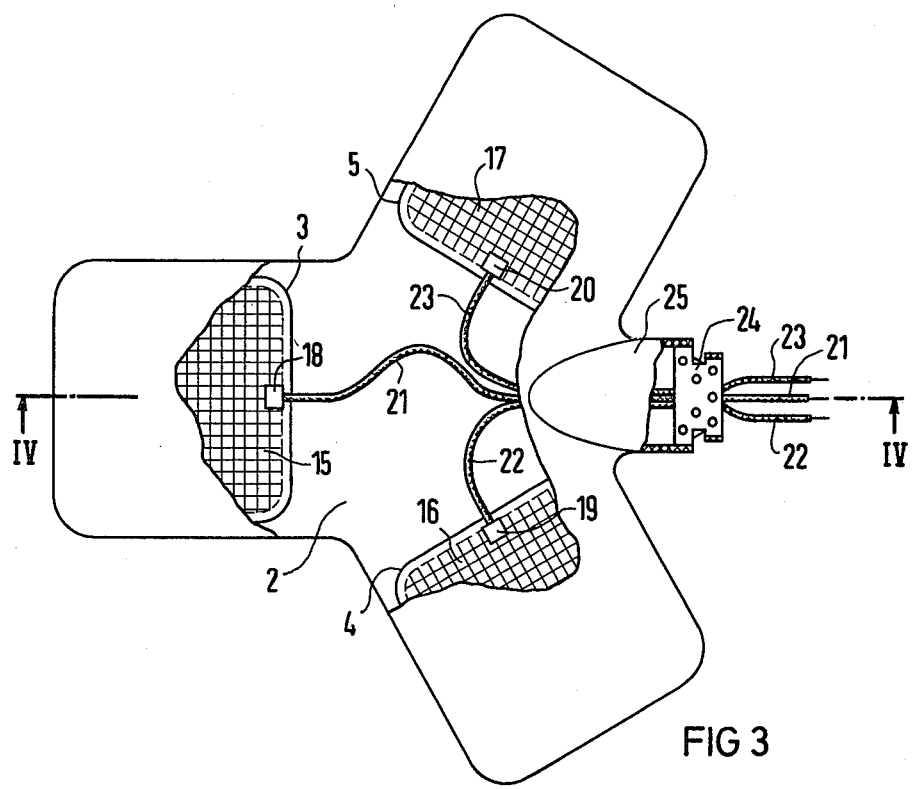
FIG. 3 illustrates a plan view of the opposite side of a star electrode system according to FIG. 1, in a partially cut-open state.
Figure 5:
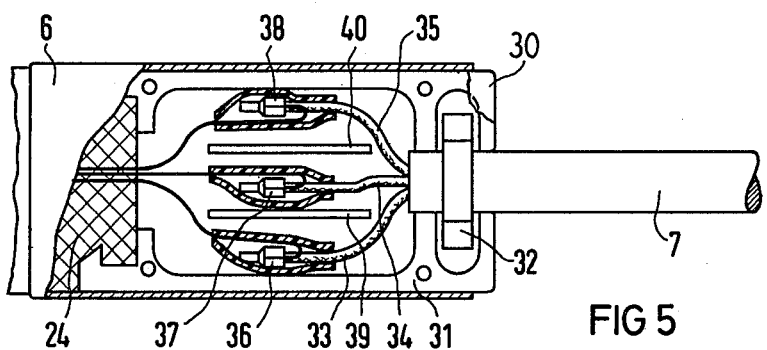
FIG. 5 illustrates a cross section of a coupling part as electrode connection.

FIGS. 1 and 2 are illustrated to a reduced scale while FIGS. 3 and 4 are approximately to the natural scale for an exemplary embodiment; FIG. 5, by contrast, is illustrated enlarged.

Identical parts of the figures are provided with the same reference characters.

In FIG. 1, 1 designates a star electrode system with a formed part 2 consisting of electrically insulating plastic which is composed of three square (or quadratic) lobes in star formation which are respectively offset from each other by 120°. The edges of these lobes are slightly rounded, whereby a square (or quadratic) contact part 3, 4 or 5 is inserted in each of these lobes. Between contact parts 4 and 5, a coupling part 6 as line connection is secured on the formed part 2. The construction of the line connection shall be explained in greater detail below. Via an operating cable 7 with an operating plug 8 the electrode system is connectable to a (nonillustrated) stimulation current operating apparatus.

In FIG. 2 an electrode system is designed as a band-electrode configuration 9 comprising a formed part 10 of electrically insulating plastic into which approximately triangular contact parts 11, 12 and 13 are tandem-joined such that the centroids of the triangles, offset relative to one another, again form a triangular shape. An operating cable connection 14 is here designed as a plug-in coupling.

In FIG. 3 the upper side of the plastic flat part 2 according to FIG. 1 is shown. In the partly broken-away showing of the formed part 2 in FIG. 3, the noncontacting upper sides of the contact parts 3, 4 and 5 are visible. Wire nettings 15, 16 and 17 are applied on these noncontacting sides, respectively. The wire nettings essentially serve the purpose of improved current distribution over the entire area of the application surfaces of the conductive contact parts 3, 4 and 5. The wire nettings 15, 16 and 17 have respective connections 18, 19 and 20 from which electric lines 21, 22 and 23 are each conducted to a coupling part 24 as connection. The electric lines 21, 22 and 23 are shown as having sufficient length so that slack is present in each line between its connection points at 18-20 and 24. In the region of the connection part 24 the plastic formed part 2 is provided with a thickened construction (as indicated at 25 in FIGS. 3 and 4) for the purpose of improved stability.

The construction of the electrode system of FIGS. 1 and 3 is further illustrated by the sectional view of FIG. 4.

In order to manufacture an electrode system of this type, a wire netting with a connection line is first connected in a form, by means of thermal treatment, with a conductive silicon rubber in a prescribed surface-configuration which is somewhat greater in area than the wire netting, so that on one side of the silicon rubber a completely smooth surface results. The conductive inserts thus prepared are then fitted into a form (or mold) and connected by means of heating with the electrically nonconductive plastic. Through vulcanization a completely sealed (or tight) connection results at the boundary surfaces between the conductive plastic and the insulating plastic. This is, in particular, advantageous since, in this fashion the electrode system can be cleaned and sterilized as a whole after use. The connection lines 21 through 23 of the contact parts 3 through 5, in Teflon coverings (or sheathings), are embedded during the thermal treatment in a loop-formation in the nonconductive plastic such that the flexibility of the entire electrode system is not impaired and the lines themselves are not subjected to stress (or pull). The conductive contact parts expediently exhibit a continuous spline beading, as a consequence of which, during vulcanization of the contact parts 3–5 into the insulating support part 2, the mechanical securing in the insulating plate is further improved.

Since the actual operating cable 7 (FIGS. 1, 4) for the purpose of connection to an operating apparatus expediently consists of flat wire conductors, it is necessary to design the line connection to the formed part 2 as a coupling part. This can be designed either as a crimp-connection, or as a plug. In FIG. 5, a coupling part is illustrated as a fixed (or rigid) connection. It consists of two half-shells 30 and 31 which, on the one side, are capable of being placed on the connection 24 according to FIG. 3, and, on the other side, exhibit a recess for a pull (or tension) relief element 32 of the operating cable. The individual lines 33 through 35 of the operating cable are connected with the lines 21 through 23 in this housing, formed in this fashion, via crimp-connections 36 through 38. Strips or cross pieces 39 and 40 serving as insulation parts are arranged between the individual crimp-connections 36 through 38.

The design and preparation of the inventive electrode arrangement described above by way of example for a star electrode can be transferred to the integration of individual electrodes of random number and random arrangement. It is advisable here to adapt surface-configuration and size to the various application purposes, whereby such systems can be readily exchanged, possibly via the coupling part.

For application of the inventive electrode arrangement, it has proven expedient to place the entire component part into an electrode pocket which consists, on the application side, of a fleece material and, on the back side, of a plastic sheet. The fleece material is moistened during application, whereby, in this fashion, the contact resistance of the electrode contact parts to the skin is reduced. Undesired transverse displacement (or shunting) currents between the electrode fields are negligibly small with utilization of fleece materials of minimal thickness. Altogether, due to good flexibility, softness and snug (or close) contactibility of all employed materials, an unproblematical emplacement and fixation of the inventive electrode system on the patient's body thus results.

It will be apparent that many modifications and variations may be effected without departing from the scope of the novel concepts and teachings of the present invention.

A commercial instrument known under the trademark "STEREODYNATOR" is described as producing stereodynamic interferential current with the aid of three five-kilohertz electric fields which are applied to the body using only two star-shaped, highly flexible electrode systems in an article entitled "Sterodynamic Interferential Current Therapy-Fundamentals and Initial Results", by H. Thom, M.D., in *Electromedica*, No. 1, 1980, pages 18–20.

We claim as our invention:

1. An electrode system for supplying electric signals to a body surface of a patient, said system comprising an electrode arrangement including a housing, electrode contact means supported by said housing for emplacement in conforming relation to the body surface of the patient for supplying electrical signals to the patient, and electrical line means electrically connected to the electrode contact means and leading from the housing for electrical connection with an interference current apparatus, or the like, said electrode arrangement having an extended area frontal face for disposition in confronting conforming relation to the body surface of the patient, the housing being an extended area flexible generally flat formed layer of electrically insulating plastic; said electrode contact means comprising flexible electrically conductive layers of extended area generally flat configuration having extended area interior surfaces within the housing and extended area exterior surfaces disposed exterior to the housing and separated by a thickness dimension from the extended area interior surfaces; flexible wire webs of electrically conductive material and of generally flat extended area configuration and of area substantially corresponding to the area of the interior and exterior surfaces and being embedded at the interior surfaces so as to be separated from said exterior surfaces of said flexible electrically conductive layers, said flexible wire webs being connected with said electrical line means such that electric signals are supplied from the electrical line means to the wire webs and from the wire webs through the thickness dimension of the flexible electrically conductive layers to substantially the entire area of the exterior surfaces of said flexible electrically conductive layers; said flexible electrically conductive layers (3–5, 11–13) being of material sealable with said electrically insulating plastic and being embedded flatwise in said generally flat formed layer (2, 10) of said electrically insulating plastic in such a fashion that the exterior surfaces of the flexible electrically conductive layers and adjacent surfaces of the generally flat formed layer of said electrically insulating plastic are continuously sealed to each other at their boundaries and such that said electrode arrangement as a whole has a substantially constant flexibility over the entire extent thereof which is to be conformed to the body surface.

2. An electrode system according to claim 1, with said electrically conductive layers comprising contact parts (3–5, 11–13) with respective exterior surfaces forming said exterior surfaces of said electrically conductive layers and projecting beyond the adjacent surfaces of the formed layer (2, 10) of said electrically insulating plastic.

3. An electrode system according to claim 1, with said electrically conductive layers comprising electrode contact parts (3, 4, 5) forming a triple electrode, the formed layer (2) of said electrically insulating plastic having a star-shaped surface with lobe-shaped parts which are offset 120°, respectively, which each support a contact part (3, 4, 5), the contact parts being continuously sealed to the respective lobe-shaped parts.

4. An electrode system according to claim 3, with the lobe-shaped parts being approximately square and exhibiting rounded corners.

5. An electrode system according to claim 1, with the electrically conductive layers comprising contact parts (11–13), and the formed layer (10) of said electrically insulating plastic being band-shaped and joining the contact parts (11–13) in tandem.

6. An electrode system according to claim 5, with the electrically conductive layers comprising contact parts (11–13) having approximately triangular surfaces and being inserted with the centroids alternately oppositely offset in the band-shaped formed layer (10) of said electrically insulating plastic.

7. An electrode arrangement according to claim 1, with the electrical line means comprising connection lines (21–23) connected to the wire webs of the electrically conductive layers (3–5, 11–13); having polytitrafluoroethylene coverings and being sealed into the formed layer (2, 10) while laid out along paths with loops therein.

8. An electrode system according to claim 1, with a coupling part (24) arranged on the formed layer (2, 10), and having a common cable (7) connected therewith and comprised of said electrical line means.

9. An electrode system according to claim 8, with the coupling part (24) having a pull relief (32) for the cable (7).

10. An electrode system according to claim 8, with the cable (7) being in the form of a flat wire cable which is connected in the coupling part (24) with the electrical line means (21–23) of the electrically conductive layers (3–5) by means of pinch connections.

11. An electrode system according to claim 1, with a coupling part of the formed layer (10) being in the form of a plug and socket type connector.

12. An electrode system according to claim 1, with said electrically conductive layers comprising electrically conductive plastic parts (3–5 11–13), and said flexible wire webs comprising wire gauze (15–17) embedded in the respective electrically conductive plastic parts (3–5, 11–13).

13. An electrode system according to claim 1, with said flexible generally flat formed layer of electrically insulating plastic and said flexible electrically conductive layers means being tightly sealed through vulcanization.

14. An electrode system according to claim 13, with said flexible wire webs being embedded at the interior surfaces of said flexible electrically conductive layers by vulcanization.

15. An electrode system according to claim 1, with said electrically conductive layers comprising electrically conductive plastic parts, and said flexible wire webs comprising wire gauze vulcanized in the respective electrically conductive plastic parts.

* * * * *